(12) United States Patent  (10) Patent No.: US 6,652,453 B2
Smith et al.  (45) Date of Patent: Nov. 25, 2003

(54) PORTABLE VIDEO LARYNGOSCOPE

(76) Inventors: Vincent A. Smith, 114 Newcastle Dr., Vallejo, CA (US) 94591; Susan V. Smith, 114 Newcastle Dr., Vallejo, CA (US) 94591

(*) Notice: Subject to any disclaimer, the term of this patent is extended or adjusted under 35 U.S.C. 154(b) by 124 days.

(21) Appl. No.: 09/954,258

(22) Filed: Sep. 10, 2001

(65) Prior Publication Data

US 2002/0022769 A1 Feb. 21, 2002

Related U.S. Application Data

(63) Continuation-in-part of application No. 09/503,440, filed on Feb. 14, 2000.
(60) Provisional application No. 60/122,716, filed on Mar. 30, 1999.

(51) Int. Cl.$^7$ .............................. A61B 1/267; A61B 1/05
(52) U.S. Cl. ...................................... 600/188; 600/194
(58) Field of Search ................................. 600/185, 187, 600/188, 194, 196, 197, 199, 190, 104, 113, 114, 120, 129, 136; 606/106

(56) References Cited

U.S. PATENT DOCUMENTS

| | | | | | |
|---|---|---|---|---|---|
| 4,126,127 A | * | 11/1978 | May | ............................ | 600/187 |
| 4,306,547 A | * | 12/1981 | Lowell | ....................... | 600/188 |
| 5,003,963 A | * | 4/1991 | Bullard et al. | ............... | 600/104 |
| 5,111,281 A | * | 5/1992 | Sekiguchi | ..................... | 358/29 |
| 5,183,031 A | * | 2/1993 | Rossoff | ....................... | 600/131 |
| 5,363,838 A | * | 11/1994 | George | ......................... | 600/120 |
| 5,381,787 A | * | 1/1995 | Bullard | ......................... | 600/188 |
| 5,827,178 A | * | 10/1998 | Berall | ........................... | 600/185 |
| 5,841,491 A | * | 11/1998 | D'Alfonso et al. | ........... | 348/65 |
| 6,071,233 A | * | 6/2000 | Ishikawa et al. | ............. | 600/104 |
| 6,350,235 B1 | * | 2/2002 | Cohen et al. | ................ | 600/199 |

* cited by examiner

*Primary Examiner*—Eduardo C. Robert
*Assistant Examiner*—David C Comstock

(57) ABSTRACT

A laryngoscope for use in intubating a patient's trachea, in routine and emergency situations. The laryngoscope has a camera mounted in the vicinity of a distal end of its probe to observe the patient's trachea opening and transmit a signal to a display on the handle. The distal end of the probe also includes ovoid, generally C-shaped gripping means, a pair of elongated grasping lips on the gripping means, and an internal clamping assembly for controlling the gripping means.

9 Claims, 5 Drawing Sheets

PORTABLE VIDEO LARYNGOSCOPE

RELATED APPLICATION

This is a continuation-in-part of Ser. No. 60/122,716 filed Mar. 30, 1999, titled "Smith Video Laryngoscope" by Vincent A. Smith and Susan V. Smith and Ser. No. 09/503,440, filed Feb. 14, 2000 for "Portable Video Laryngoscope", by Vincent A. Smith and Susan V. Smith.

FIELD OF THE INVENTION

This invention relates generally to laryngoscopes and more particularly to a laryngoscope that is battery powered, having an ergonomic pistol grip, flexion control, a biopsy port, suction on demand, oxygen and medication infusion capabilities, a video camera chip and objective lens and an associated lightweight portable LCD screen. The video laryngoscope is particularly useful in a procedure for intubating a patient's trachea, in routine and emergency situations.

BACKGROUND OF THE INVENTION

In the medical field, intubation is the process of putting an Endotracheal (ET) tube into a person's throat to maintain the airway either for emergency breathing, or for the delivery of oxygen and anesthetics.

Fiberoptic intubating instruments having a display and a camera are known and disclosed in patents including U.S. Pat. No. 5,827,178 to Jonathan Berall, U.S. Pat. No. 5,363,838 to Dr. Gordon George and U.S. Pat. No. 4,742,819 to Dr. Gordon George. Fiberoptic intubating instruments having a fiberoptic bundle, objective lens and an eyepiece are typified by patents U.S. Pat. No. 4,086,919 to Bullard and U.S. Pat. No. 5,183,031, to Rossoff.

U.S. Pat. No. 5,363,838, Berall teaches a laryngoscope that is similar in shape, configuration and construction to a common manual laryngoscope except that it has a view screen that would hinge on the side of the cylindrical body of the laryngoscope and a camera on the end of the laryngoscope blade to provide continuous visualization of the operating field as an adjunct to directly visualizing the pharynx. Berall also teaches that the monitor is mounted lower on the handle, close to the blade of the laryngoscope and to be along the same line of sight to the patient's throat, so that the professional intubator's direct view of the patient's larynx and simultaneous view of the screen can be achieved with no head movement. Berall also describes a laryngoscope configured to the shape of a common laryngoscope blade that does not employ any controllable ET tube gripping means. He further states that while the left hand passes the laryngoscope blade behind the base of the tongue and into the pharynx, the instrument for passing the endotracheal tube is passed conventionally using the intubator's left hand, the convention being, having a rigid laryngoscope blade and using a stylet reinforced ET tube inserted manually. Berall also describes a blade configuration that is rigid, having no built-in means to accomplish controlled articulation. The only controls cited are an on/off switch. Berall makes no claims as to open working channels on his laryngoscope to enable suction capabilities, medication or oxygen infusion, or biopsy procurement. The peripheral components of the conventional intubation procedure, including, but not limited to, suction, oxygenation and/or specimen removal are normally separate from conventional laryngoscopes and thus require separate tools.

U.S. Pat. Nos. 4,742,819 and 5,363,838 to Dr. Gordon George teaches a fiber optic intubation system, where a conventional laryngoscope is employed to directly visualize and open the airway of a patient, while a fiberoptic camera probe is passed into the throat for indirect visualization of the operating field on a separate LCD screen. The LCD screen is not integrated to the probe/camera, but communicates fiber optically from lens to the camera, and then electrically, via video cable from the camera to the separate monitor. The fiberoptic system is separate from the laryngoscope. Dr. George teaches that the probe is a semi-malleable tube that can be pre-shaped prior to insertion, and has a manipulating lever to provide flexion control. The semi-malleable tube also serves as a stylet. In conventional intubation, the stylet is a semi malleable wire that when inserted inside the ET tube, provides stiffness to reinforce and enhance maneuverability the otherwise soft and pliable ET tube for manual deployment and proper placement of said tube by the user. Dr. George does not teach any obvious controllable ET tube grasping or deployment means, nor is any grasping means necessary with the stylet technique. Dr. George teaches that the probe has a camera in the proximal end of the probe and the distal end has a lens with fiber optic means of communication to the camera, which is connected to a separate view screen. Dr George does not teach any integrated means of oxygen, medication, or suction delivery, anyone familiar with the art will recognize that the aforementioned capabilities exist as separate systems during conventional intubation. Further, Dr. George describes the intubation procedure conventionally, where separate tools are needed for suction, oxygenation and medication delivery.

U.S. Pat. No. 4,086,919, Bullard discloses a rigid fiberoptic laryngoscope with a single eyepiece that is illuminated by a fiber optic system. Bullard claims movable, grasping jaws designed to grasp hold and release an ET tube, with moveable extension means to advance the tube. The said grasping means resembles an endoscopic biopsy forceps in design, is removable and housed in an open conduit, or working channel, that is an open tube extending from one end of the probe to the other. The only work Bullard claims for the working channel is to provide a conduit for the grasping device. Oxygen, suction or medicine administration is never claimed, and cannot be done with a grasping tool inserted into and thus occluding, the working channel tube. The forgoing E.T. tube grasping system is not integral to the body of the laryngoscope.

U.S. Pat. No. 5,183,031, Rossoff claims medication, oxygen and suction capabilities in a fiberoptic laryngoscope with a single eyepiece and a pistol grip configuration, very similar in design to a bronchoscope. He further discloses his design to be used in the manner of a stylet, which is inserted into the ET tube for manual deployment by the Intubator. The inherent weakness of this design is that in order for the probe to be able to pass the "goose neck" stylet into the internal lumen of the ET tube, it needs to be of a very small diameter. The standard adult sized 8.0 endotracheal tube has an internal diameter of ¼ inch. Therefore, anyone skilled in the art would know that the stylet diameter and the diameter of the oxygen and suction ports correspondingly, must be of a very small diameter, similar to the design of a bronchoscope. Bronchoscopes generally have an external diameter of ⅛ inch and are well known to have very limited suction and infusion capabilities, inadequate for intubation. Bronchoscopic suction and oxygen capabilities, while adequate for visualization of the bronchial pathways of the lungs, are very limited and cannot handle the large volumes necessary to remove copious oral secretions or mucus, or to provide the volumes of Oxygen necessary to push open an airway or to oxygenate a patient. When a bronchoscope is used for intubation, separate suction and oxygen delivery systems are always used.

U.S. Pat. No. 5,841,491 to D'Alphonso et al, describes a fiber optic scope enhancement system that employs a digital to analog, and analog to digital converters, also known as a D/A and A/D converters respectively, to enhance images acquired by an analog camera that receives images that have been distorted by the fiber borders of a fiber optic bundle. In order to process analog images in a digital image filter, the analog images must be digitized by the A/D converter, then processed digitally, then converted back to analog by the D/A converter for eventual display by the analog television monitor. While this system of using A/D and D/A conversion may be necessary for image enhancement of analog images captured via a fiber optic bundle, it is unnecessary with a system receiving digitally acquired images that have not been distorted by a fiberoptic imaging system. The D/A conversion unit is only necessary to display digitally acquired images on an analog television or LCD monitor.

U.S. Pat. No. 4,306,547, by Lowell describes a rigid laryngoscope incorporating an instrument-supporting channel that is an open, U-shaped in cross section and is the only open channel available to the user to insert separate tools, E.T. tubes, or to extract samples for diagnosis or biopsy. Thus, anyone familiar in the art, would recognize that the separate processes of intubation, suction, specimen retrieval, must be done separately while using a single instrument supporting channel.

The main weakness of the aforementioned systems is that, when a fiberoptic objective lens on the tip of a laryngoscope is inserted into a patient's throat, it contacts either oral secretions or mucus coating the soft tissues of the throat, which adheres to the lens surface and either distorts, or obscures the optical lens view of the operating field. The described systems do not employ controlled suction capabilities; to remove said oral secretions or foreign bodies, which can obstruct the visual field. Nor do the aforementioned systems provide continuously flooding oxygen into the operating field in order push away the soft tissues form the probe surface and blow over the optical lens surface to clear oral secretions from the lens of the camera, thus preserving the unobstructed view of the operating field.

Nor do the aforementioned intubation systems address the most ominous aspect of intubation, hypoxia and/or anoxia, which anyone familiar to the art knows, that the human brain can tolerate only up to six minutes of oxygen deprivation before it starts to die. By using a system employing a flood of pressurized oxygen to open the airway and visualize the operating field, some of the oxygen being infused into the larynx will diffuse into the lower respiratory tract and provide oxygen to the patient who is at risk for hypoxia. Oxygen deprivation, brain damage, and death are the most serious consequences of a failed intubation.

Another weakness shared by the all of the forgoing systems is that the designs are not compact and multitask capable, in that there is no integrated capability for simultaneous oxygenating, suctioning, medicating and intubating a patient. The ability to remove secretions, blood, or foreign substances, to provide oxygen to a patient, or the ability to infuse irrigants or medications, have traditionally required an interruption of intubation and removal of the laryngoscope to apply the separate tools capable of providing these functions, which results in prolonging the time it takes to accomplish the act intubation in the clinical setting.

Another weakness shared by the aforementioned systems is that they do not employ an integrated, user controlled, ET tube guidance and deployment system. A user controlled, ET tube guidance and deployment system enables the Professional Intubator a greater degree of control during ET tube placement and deployment. The handle mounted control switch of the guidance system, when depressed, can be pressed all the way down to open the ET clamps and detach the ET clamps from the ET tube allowing for full deployment. When the handle control switch is pressed gradually by the user's first hand, the ET clamps loosen gradually, forming a variable grip ET tube guiding channel. This capability allows the Professional Intubator to hold the ET tube tightly during insertion into the operating field and then to guide the tube in the right direction with a push provided by the user's other hand eliminating the need for a stylet. The internal workings of the guidance system utilizes a sealed, internal channel housed in the Laryngoscope handle and the blade to allow manipulation of cables connected to the control switch to manipulate the ET clamps.

SUMMARY OF THE INVENTION

Objects of the Invention

It is an object of this invention to provide a specialized laryngoscope capable of also serving as the intubating instrument in a procedure for intubating a trachea of a patient, especially a patient whose pharynx, larynx and trachea are not easily visualized.

A further object is to provide such a laryngoscope, which is user-friendly to the Intubator.

A further object is to provide an electronic laryngoscope with digital camera and LCD display screen, which provides continuous indirect visualization of the operating field during the intubation procedure.

A further object of the invention is to provide such a laryngoscope, which can be set up quickly and easily.

A further object of this invention is to provide such a laryngoscope, which is self-contained, lightweight and portable.

further object of this invention is to provide such a laryngoscope with the capability of infusing intratracheal medications such as Narcan, Lidocaine, Atropine and Epinephrine, per Advanced Cardiac Life Support (ACLS) protocol.

A further object of this invention is to provide such a laryngoscope with the capability of infusing irrigation fluids, such as saline or other water solutions.

A further object of this invention is to provide such a laryngoscope with controllable suction on demand capabilities to remove blood, secretions and foreign bodies simultaneous with the intubation procedure.

A yet further object is to have the ability to infuse oxygen to the patient, simultaneous with the intubation procedure.

A yet further object is to combine and improve upon aspects of prior Endoscopic and Laryngoscopic systems to create a unique instrument incorporating the strengths of these systems and eliminating the weaknesses of the aforementioned systems.

Yet another object to have alternatively designed probes to allow use with such other body cavities as the lungs, stomach, vagina, ears and anus.

These and other objects and advantages will be apparent to those skilled in the art in light of the following disclosure, claims and accompanying drawings.

DESCRIPTION OF PREFERRED EMBODIMENT

Figure 1:
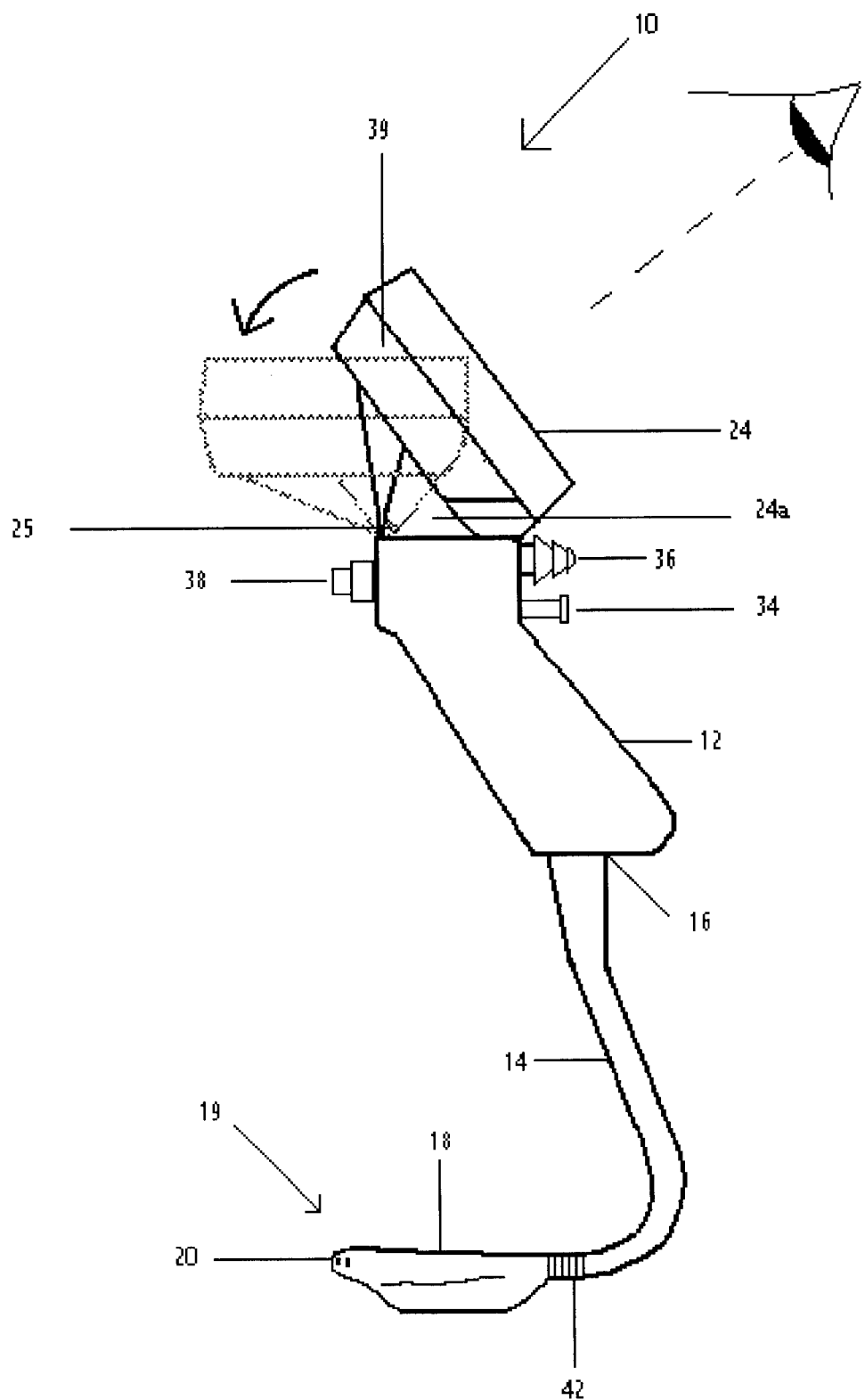
FIG. 1 is a left side view of a laryngoscope of the invention not to scale.
Figure 2:
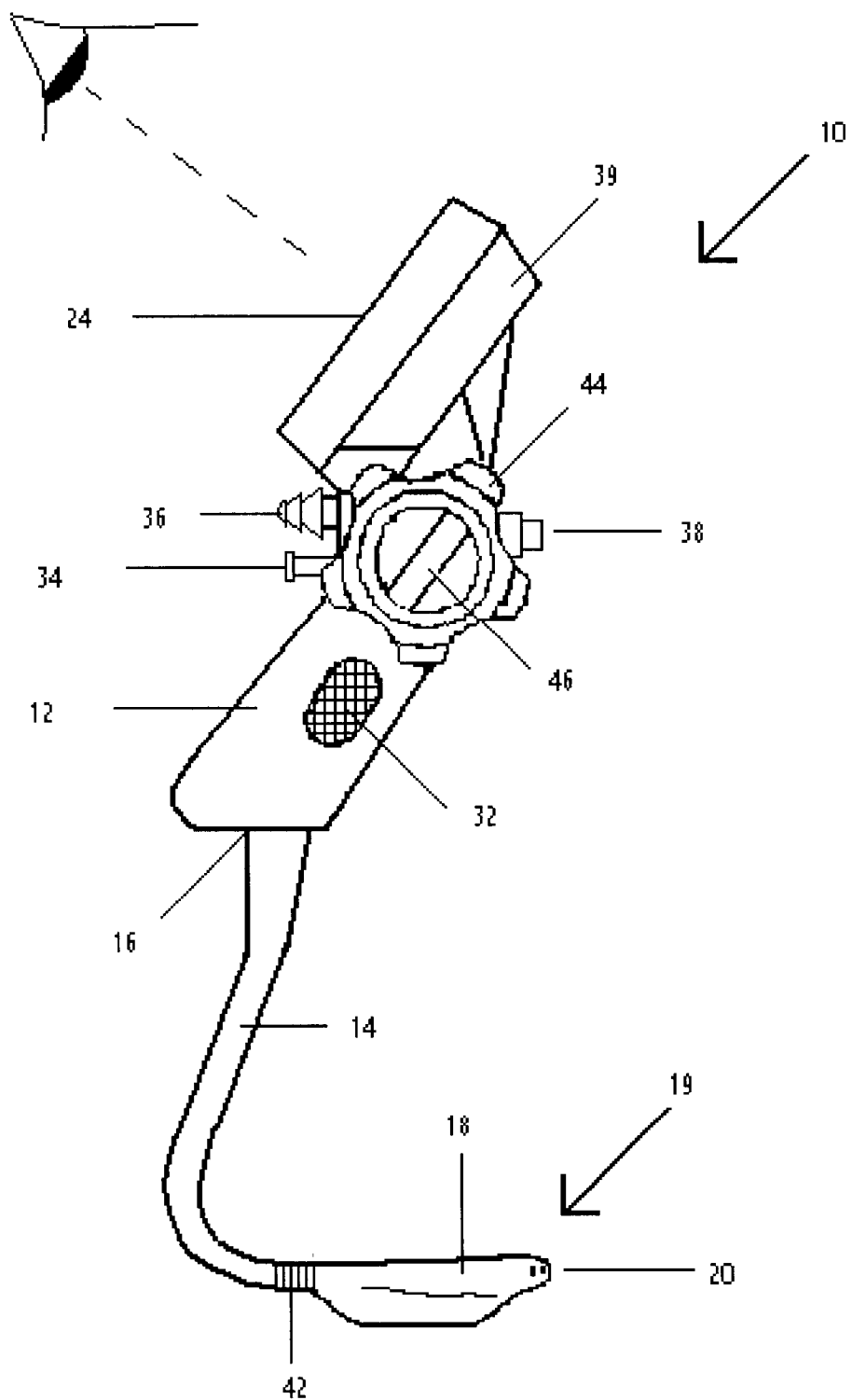
FIG. 2 is a right side view of a laryngoscope of the invention not to scale.
Figure 3:
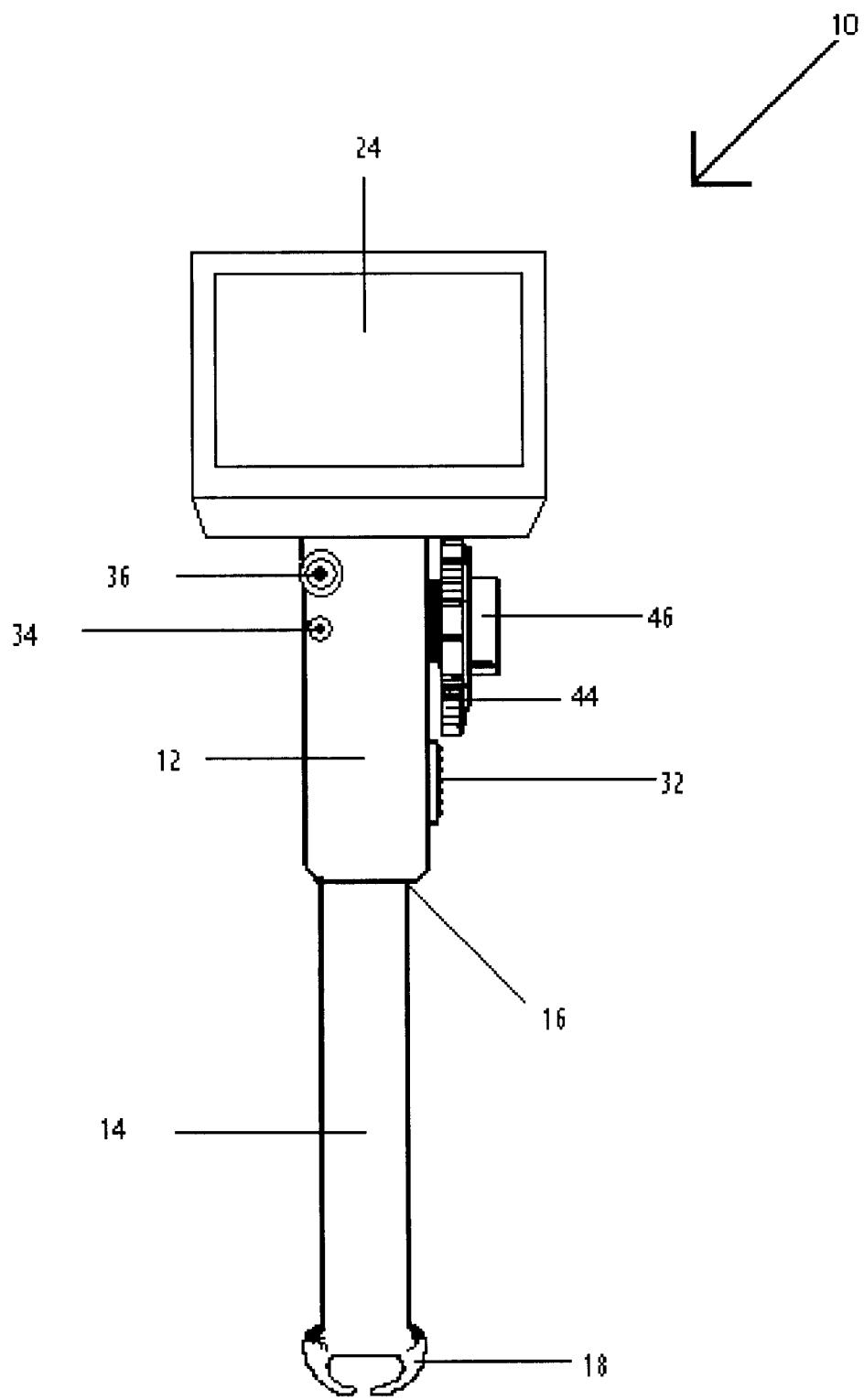
FIG. 3 is a front view of a laryngoscope of the invention not to scale.

Referring to FIGS. 1, 2, and 3, a laryngoscope 10 of the invention includes a handle 12 and a probe 14 having a proximal end 16 connected to the handle 12 and a distal end 18 projecting laterally therefrom. The probe is designed for its particular use, in this case for entering the throat area and deploying an ET tube. In other applications for other body cavities the probe should be appropriately shaped and sized.

Figure 4:
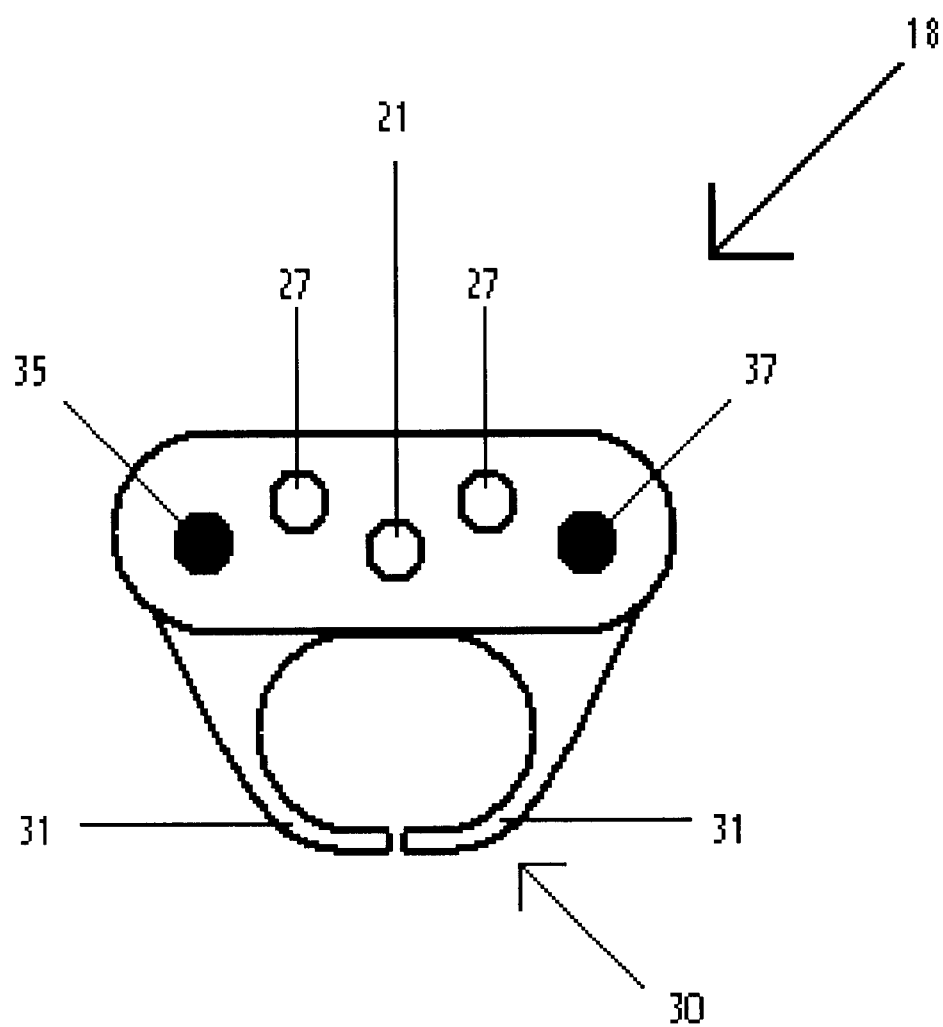
FIG. 4 is a front view of an alternative distal end of a probe of the invention not to scale.

An information gathering means 19, including a camera means 20 is mounted on the laryngoscope 10. The camera means 20 including lens 21 (FIG. 4) located in the vicinity and as close to the distal end 18 of the probe 14 as possible or along the probe 14, or if necessary on the handle 12 for observing a visual field adjacent the distal end 18 of the probe 14. A display means 24 is hinged about an axis 25 to be adjustably mounted on the handle 12 to allow adjustment for best viewing when manipulating the laryngoscope 10. The display is operatively connected to the camera means 20 to receive the signal to display the visual field as observed by the camera means 20. Preferably, the camera means 20 is internally connected to the display means 24 via a digital to analog converter 24a located within the compartment of the display means 24. The information gathering means 19 also includes light emitters 27 (FIG. 4) in the vicinity of and as close to the distal end 18 of the probe 14 as possible or along the probe 14, or if necessary on the handle 12 with the light conveyed to the distal end of the probe 18 via a fiberoptic light bundle, to illuminate the visual field in the area adjacent the distal end 18 of the probe 14 so that camera means 20 produces a usable image.

The laryngoscope 10 is equipped with a grasping clamp means 30 (see FIG. 4) on the probe 14 in the vicinity of the distal end 18 for releasably holding an ET tube. The clamp means 30 includes lips 31 and a control button 32 for manipulating and controlling the lips 31. Control button 32, is accessible on the handle 12.

Figure 5:
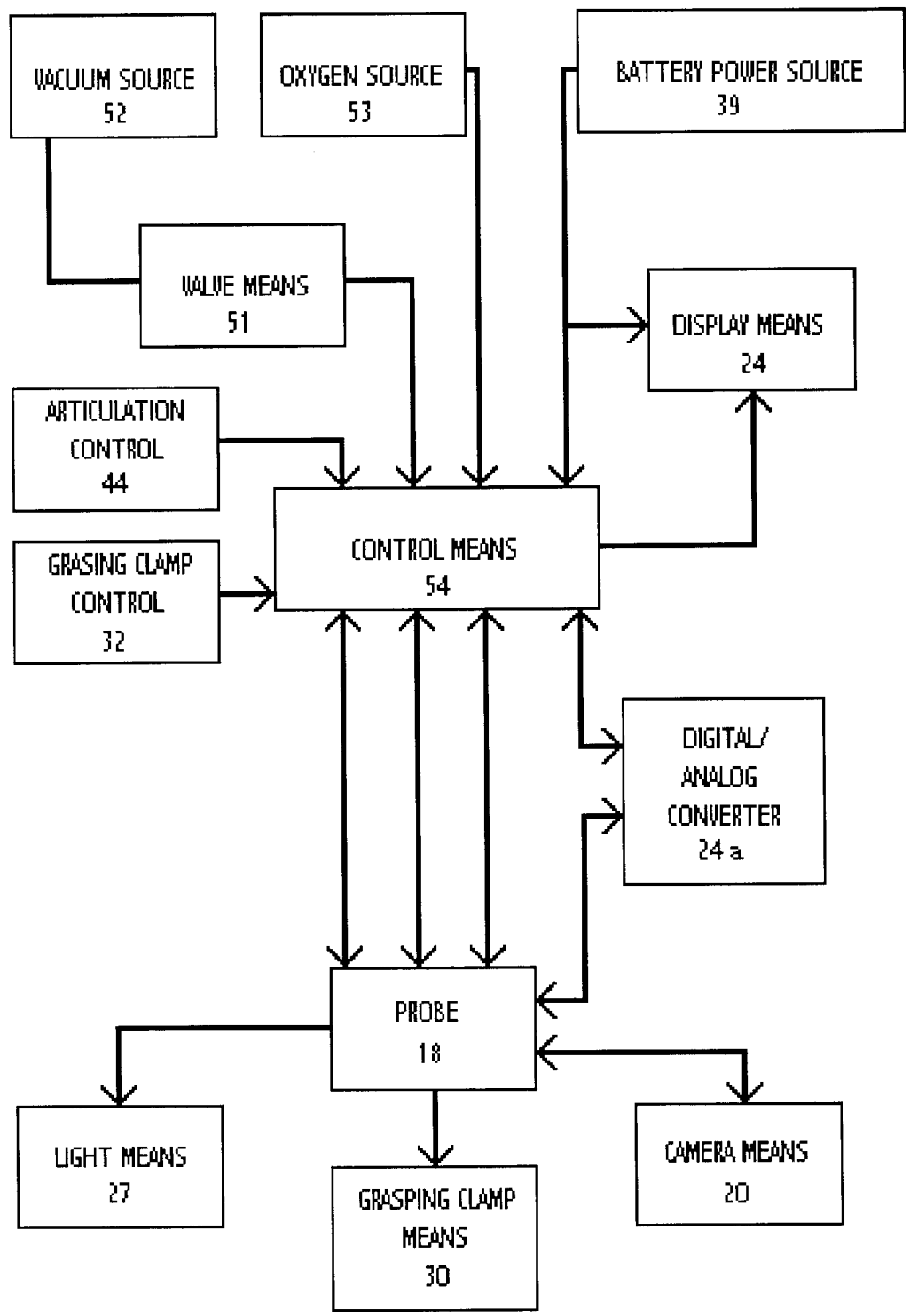
FIG. 5 is a block diagram schematic showing elements of the invention.

The handle 12 and probe 14 preferably have one or more internal channels or tubes to provide flow communication on demand between the handle 12 and proximal end 16 and the distal end 18 of the probe 14 for multiple purposes including delivery of oxygen containing gas. The channels originate at the handle with an infusion port 34 and suction port 36 which communicate respectively with an infusion port 35 and suction port 37 at the distal end 18. Purposes for the channels include introduction of oxygen 53 (see FIG. 5), medications, or irrigation fluids via infusion port 34 to the area adjacent to the distal end 18, or for the suctioning of fluids and particles from the area adjacent to the distal end 18 from a vacuum source 52 (see FIG. 5) connected to suction port 36 and controlled by suction control means 54 and valve means 51 (see FIG. 5). Other purposes for the channels include the introduction of endoscopic tools into the intake port 34 and channeled to the distal end 18 and out of infusion port 35 (FIG. 4), either to obtain biopsies, or to treat the operating field. The handle 12 also includes a suction control button 38 to provide means for turning on and off the suction and adjusting the strength of the suction along the suction channel via control means 54 utilizing valve means 51 (see FIG. 5).

The handle 12, has a compartment in which the following elements are provided (See FIG. 5):

i. Battery power supply means 39 for powering camera means 20, light means 27, control means 54, D/A converter 24a, display means 24.

ii. Control means 54, having both electrical and mechanical functions for controlling suction valve means 51, light means 27, distal probe tip 18, D/A converter 24a, display means 24, grasping clamp means 30.

iii. Mechanical controls to control the articulation 44 of the distal probe tip 18 and endotracheal tube grasping clamp control 32 to control the grasping clamp means 30.

iv. Vacuum source 52.

v. Oxygen source 53.

The probe 14 also includes a controllable pivot point 42. Control of the pivot point 42 is provided by a flexion control wheel 44 with control lock 46 to provide a flexion control means to articulate the probe head 18 up and down to adjust the best visualization for the display means 24.

Additional details include describing the optical scope as a lightweight, self contained, hand held scope made of plastics, rubber and electronics, weighing less than a pound, or ½ kilo. The display means 24 can be a small, removable LCD monitor. A removable, rechargeable, Nickel-Cadmium battery 39 can provide the power for the said laryngoscope 10.

A suitable infusion port 34 is provided by a threaded (Luer Locked) port, which will also accept the threaded nipple of a hypodermic syringe. This can allow, if dictated by the circumstances, the tracheal infusion of drugs in liquid form, such as Lidocaine, Narcan, Atropine and Epinephrine. Biopsy brushes and other endoscopic tools can also be inserted at this port 34 for obtaining biopsies of the larynx or throat. The infusion port 35 can also infuse irrigation solutions, either to clean the lens 21 of the camera means 20, or to wash away blood, mucus, gastric fluids or any other substances that the subject may have ingested. By attaching oxygen tubing connected to an oxygen source to the infusion port, 100% concentration oxygen can be delivered continuously into the patient's airway during intubation, thereby, reducing oxygen deprivation and hypoxia.

The suction port 36 can be a cone shaped metal head that connects to plastic suction tubing from a suction source and thus provides suction to the suction port 37 at the distal end of the probe 18. With use of the suction valve button 32 secretions, blood, or any other fluids that hinder the view of the camera lens 21 can be transported away from the site. This suction capability has the added benefit of being able to attach the scope surface against the surface of (or "suck up to") a foreign body for the purpose of extraction. If desired, the suction port 36 will accept standard oxygen tubing being mated to it. This way, the practitioner can use the control valve 39 to give the subject a burst of pure oxygen when needed during intubation, thereby, reducing oxygen deprivation and hypoxia. Another variation of this system would be to manufacture the handle with a separate Oxygen control valve to allow for a "burst" capability.

The distal end of the probe 18 is ovoid in cross section. The ovoid probe is approximately 8 inches long, with a 90-degree curve, and 1 inch wide and ⅜ inch thick in the adult model (other options would be to create various sizes, Adult, Pediatric and a "Preemie" pediatric model).

Beneath the ovoid head there are a pair of pliable rubber grasping lips 31 about an inch long, to hold and guide the ET tube for advancement into the larynx. There is an internal clamping assembly for the ET tube clamping mechanism to force the grasping lips together to hold onto the ET tube for placement. ET tube deployment would be achieved when the ET tube is pushed forward manually, with the practitioner using the ET clamp control to open the rubber lips 31 of the ET tube clamp assembly 30, releasing the ET tube and forming a channel, guiding the ET tube to its proper position.

It is not intended that this description be a limitation on this optical scope. This system is adaptable for medical or industrial endoscopic use, endoscopes, bronchoscopes, sigmoidoscopes, colonoscopes, laparoscopes, otoscopes and vaginal speculums. Other versions of this device are possible, such as a disposable blade version. However, in a disposable blade version, the electronics and camera chip will be housed in the handle, with a socket to accept the disposable blades that would contain a fiber optic assembly and objective lens. By replacing the laryngoscope blade with an appropriate extension probe such as flexible fiberoptic colon, sigmoid, or bronchoscope tubes, otoscopic probe or a vaginal speculum blade, other uses are possible.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiments of the herein disclosed invention are meant to be included as come within the scope of the claims.

Further objects and advantages of the regenerative system will become apparent from consideration of drawings and the ensuing description of the device.

Operation

To use the laryngoscope 10, the patient is prepared, placed in a supine position with the practitioner working from the head of the table. An assistant to the intubator oxygenates the subject (using a bag-mask device delivering 100% oxygen to the patient) to help prevent hypoxia. The device 10 is turned on, with the monitor displaying 24 what the camera lens 21 "sees". The scope 10 is then attached to suction and oxygen lines with the flow levels turned on. The insertion probe 14 is passed into the mouth to the back of the throat. Oxygen flow is transmitted via the infusion port to the tip of the laryngoscope probe. The gas pressure of the oxygen flow pushes back the soft tissues of the throat and flows over the camera lens to obtain an unobstructed view of the operating field and to prevent secretions form accumulating on the lens. The Oxygen will also diffuse into the patient's respiratory tract, thus alleviating hypoxia. The infusion port accepts standard oxygen tubing and is also Luer locked, that is, configured to accept medical syringes for the infusion of irrigants or medications into the operating field. Any secretions, blood, or foreign bodies encountered by the probe can be suctioned, or removed on command via the suction control. The flexion control wheel is used to negotiate around the tongue and into the Larynx and also to acquire visualization of the operating field in the presence of anatomical deformities in the patient. When the Vocal cords are seen, the ET tube is released by the handle mounted, ET deployment clamp control switch. When this switch is depressed, it has a variable control capability and if pressed all the way down, will open the ET clamps and deploy ET tube. When the control switch is pressed gradually to loosen the clamping mechanism, the ET clamps form a loose, guiding channel. This capability allows the Professional Intubator to use the video laryngoscope to hold the ET tube tightly during insertion into the operating field and then to guide the tube in the right direction and direct final deployment of the ET tube into the trachea with a push provided by the user's other hand.

The insertion probe is then pulled back and out of the patient's mouth, and the patient has been intubated. The ET tube is secured with tape or any other standard method of stabilizing an ET tube.

Intubation with a video laryngoscope is accomplished without having to lift soft tissues out of the way for direct visualization, which results in less trauma and pain for the patient. Intubation with a video laryngoscope infusing pure oxygen will help to alleviate hypoxia in the subject being intubated. By using the video laryngoscope, intubation is accomplished easily regardless of anatomical deformities, obstructions, or secretions, since the view is indirectly acquired by a variable position video probe that is controlled by the user. Intubation by video laryngoscope gives visual proof of incubation, thereby reducing the need for chest X-rays and $CO_2$ checking devices to prove proper placement of the ET tube into the trachea.

What is claimed is:

1. A laryngoscope for aiding in the examination of a patient by an observer relying entirely upon machine generated data to derive medical conclusions, comprising:

a probe and a handle, said probe having a proximal end connected to said handle and an articulating, adjustable distal end projecting therefrom, said handle including a distal end connected to said proximal end of said end probe, the distal end of the probe including generally ovoid, C-shaped gripping means, the gripping means including a pair of elongated grasping lips and an internal clamping assembly for controlling the gripping means;

information gathering means including digital camera means mounted to said distal end of said probe to generate digital machine data and display means adjustably and releaseably mounted on said proximal end of said handle and operationally connected to said digital camera means whereby a 2-D visual display is provided a human observer, said display means defining a first working position to permit line of sight insertion of said probe into the throat cavity of a patient and a second working position in which said line of sight is blocked, so said observer relies entirely upon machine generated data for to derive medical conclusions.

2. The laryngoscope of claim 1 with the addition further comprising battery power supply means for powering said machine data generating means.

3. The laryngoscope of claim 2 in which said handle has outer side surfaces shaped into a pistol grip to be grasped by one hand of the human observer and including housed control means powered by said battery power supply means.

4. The laryngoscope of claim 3 in which said control means includes a separate valve means for connecting said distal end of said probe alternately to a vacuum source and an oxygen source to enhance the examination of said patient.

5. The laryngoscope of claim 3 in which said data generating means includes light means located in the vicinity of said distal end of said probe connected to said battery power supply means through said control means for illumination purposes and an D/A converter located in said display means also connected to said battery power supply means for converting digital signals generated by said camera means to a 2-D visual display at said display means.

6. The laryngoscope of claim 3 in which said display means is a rectangularly shaped LCD screen capable of pivoting along an axis point to provide visual display of the operating field to the user in said first and second working positions and electrically connected to said battery power supply means through said control means.

7. A method of intubating the trachea of a patient by an intubator using an incubating instrument and a laryngoscope, the method comprising steps as follows:

providing the laryngoscope with a handle and a probe, the probe having a proximal end connected to the handle and a distal end projecting laterally therefrom;

inserting the probe into the patient's mouth while grasping the laryngoscope by the handle using a first hand of the intubator for steady and constant lifting and moving to one side the patient's tongue, with the second hand of the user manipulating the flexion control wheel to acquire visual capture of the patient's tracheal opening and other oral internal structures to view;

providing illuminating means for illuminating the trachea opening and other oral internal structures;

providing controls to manipulate the articulating end of the probe to secure an adequate view of the operating field;

providing an oxygen delivery means to the distal end of the probe;

providing camera means mounted on a blade of the laryngoscope in the vicinity of the distal end of the blade so that it observes a field of view that includes the patient's trachea opening and other oral internal structures;

having the camera means operatively connected to display means for viewing the field of view thereon;

introducing oxygen gas to the area of the trachea through the oxygen delivery means;

inserting the intubating instrument into the mouth of a patient using the controllable grasping means to guide and release the ET tube, while a second hand of the intubator pushes in the intubating instrument for insertion of an endotracheal tube into the patient's tracheal opening; and positioning the display means on the handle so that while the intubator inserts and manipulates the intubating instrument into the patient's trachea the intubator observes the trachea opening and other oral internal structures of the patient on the display means unaffected by the manipulating of the intubating instrument.

8. The method of claim 7, further providing suction means on demand for the removal of secretions, noxious substances and foreign bodies.

9. The method of claim 8, further providing sample means to obtain biopsies and remove polyps with endoscopic tools through the oxygen delivery means.

* * * * *